(12) United States Patent
Yamauchi et al.

(10) Patent No.: US 9,024,054 B2
(45) Date of Patent: May 5, 2015

(54) PROCESS FOR PRODUCTION OF PURIFIED O-(2,6-DICHLORO-4-METHYL-PHENYL) O,O-DIMETHYL PHOSPHOROTHIOATE

(75) Inventors: Eiji Yamauchi, Oita (JP); Ryuhei Wakita, Toyonaka (JP)

(73) Assignee: Sumitomo Chemical Company, Limited, Tokyo (JP)

(*) Notice: Subject to any disclaimer, the term of this patent is extended or adjusted under 35 U.S.C. 154(b) by 409 days.

(21) Appl. No.: 13/133,396

(22) PCT Filed: Dec. 18, 2009

(86) PCT No.: PCT/JP2009/071712
§ 371 (c)(1),
(2), (4) Date: Jun. 8, 2011

(87) PCT Pub. No.: WO2010/074277
PCT Pub. Date: Jul. 1, 2010

(65) Prior Publication Data
US 2011/0237818 A1    Sep. 29, 2011

(30) Foreign Application Priority Data

Dec. 22, 2008  (JP) .................................. 2008-325295
Jul. 31, 2009  (JP) .................................. 2009-179000

(51) Int. Cl.
*C07F 9/18*    (2006.01)

(52) U.S. Cl.
CPC ........................................ *C07F 9/18* (2013.01)

(58) Field of Classification Search
None
See application file for complete search history.

(56) References Cited

FOREIGN PATENT DOCUMENTS

| GB | 1467561 | * | 1/1975 |
|---|---|---|---|
| JP | 55-017324 A | | 2/1980 |
| JP | 56-026897 A | | 3/1981 |
| JP | 58-026806 A | | 2/1983 |
| JP | 11-322772 A | | 11/1999 |

OTHER PUBLICATIONS

Nishizawa et al., caplus an 1961:127075.*
Int'l Search Report issued Feb. 2, 2010 in Int'l Application No. PCT/JP2009/071712.
Int'l Preliminary Report on Patentability issued Aug. 9, 2011 in Int'l Application No. PCT/JP2009/071712.
Extended European Search Report issued Apr. 18, 2013 in EP Application No. 09835073.9.
Chapter 10. Thiophosphorsäure-O,O,S-triester, Part A "Herstellung": m) "durch Isomerisierung oder isomerisierende Alkylierung von Thiophosphorsäure-O,O,O-triestern"; in SASSE K (editor) "Houben-Weyl Methoden der Organischen Chemie", vol. 12, No. 2, p. 668 (Jan. 1, 1963).

* cited by examiner

*Primary Examiner* — Sun Jae Yoo
(74) *Attorney, Agent, or Firm* — Panitch Schwarze Belisario & Nadel LLP

(57) ABSTRACT

A process for producing a purified O-(2,6-dichloro-4-methylphenyl)-O,O-dimethyl phosphorothioate, the process comprising:
the first step of bringing a crude O-(2,6-dichloro-4-methylphenyl)-O,O-dimethyl phosphorothioate into contact with an acid; and
the second step of recovering the purified O-(2,6-dichloro-4-methylphenyl)-O,O-dimethyl phosphorothioate from the mixture obtained in the first step.

4 Claims, No Drawings

PROCESS FOR PRODUCTION OF PURIFIED O-(2,6-DICHLORO-4-METHYL-PHENYL) O,O-DIMETHYL PHOSPHOROTHIOATE

TECHNICAL FIELD

The present invention relates to a process for producing a purified O-(2,6-dichloro-4-methylphenyl)-O,O-dimethyl phosphorothioate.

BACKGROUND ART

O-(2,6-Dichloro-4-methylphenyl)-O,O-dimethyl phosphorothioate (hereinafter this compound is referred to as "phosphorothioate") is a useful compound as a soil fungicide.

It is known that phosphorothioate is obtained by, for example, reacting 2,6-dichloro-4-methylphenol and O,O-dimethyl chlorophosphorothioate in the presence of copper chloride in an alkali aqueous solution (See Japanese Unexamined Patent Application Publication No. 55-17324).

DISCLOSURE OF THE INVENTION

The present invention is to provide a novel process for producing purified O-(2,6-dichloro-4-methylphenyl)-O,O-dimethyl phosphorothioate.

The present application relates to the following invention.

[1] A process for producing a purified O-(2,6-dichloro-4-methylphenyl)-O,O-dimethyl phosphorothioate, the process comprising:

the first step of bringing a crude O-(2,6-dichloro-4-methylphenyl)-O,O-dimethyl phosphorothioate into contact with an acid; and the second step of recovering the purified O-(2,6-dichloro-4-methylphenyl)-O,O-dimethyl phosphorothioate from the mixture obtained in the first step.

[2] The production process according to [1], wherein the crude O-(2,6-dichloro-4-methylphenyl)-O,O-dimethyl phosphorothioate contains an aromatic hydrocarbon solvent.

[3] The production process according to [1], wherein the acid is an inorganic acid.

[4] The production process according to [1], wherein the first step is performed by mixing a crude O-(2,6-dichloro-4-methylphenyl)-O,O-dimethyl phosphorothioate containing an aromatic hydrocarbon solvent with an aqueous solution of an inorganic acid.

[5] The production process according to [1], wherein the crude O-(2,6-dichloro-4-methylphenyl)-O,O-dimethyl phosphorothioate is obtained by bringing 2,6-dichloro-4-methylphenol into contact with O,O-dimethyl chlorophosphorothioate in a solvent in the presence of copper chloride.

[6] A process for producing O-(2,6-dichloro-4-methylphenyl)-O,O-dimethyl phosphorothioate, the process comprising:

Step A of bringing 2,6-dichloro-4-methylphenol into contact with O,O-dimethyl chlorophosphorothioate in a solvent in the presence of copper chloride;

Step B of bringing the reaction mixture obtained in said step A into contact with an acid; and Step C of recovering O-(2,6-dichloro-4-methylphenyl)-O,O-dimethyl phosphorothioate from the mixture obtained in said step B.

MODE FOR CARRYING OUT THE INVENTION

Hereinafter, the present invention will be described in detail.

In the present invention, crude O-(2,6-dichloro-4-methylphenyl)-O,O-dimethyl phosphorothioate (hereinafter this is referred to as "crude phosphorothioate") is a mixture which contains O-(2,6-dichloro-4-methylphenyl)-O,O-dimethyl phosphorothioate (hereinafter this compound is referred to as "phosphorothioate") and one or more impurities.

Examples of the impurities include by-products produced during the manufacture of phosphorothioate, impurities in the raw materials, and the auxiliary raw materials used for the manufacture. The content of at least one impurity in crude phosphorothioate is about 100 ppm or more.

Crude phosphorothioate may be in any form of a powder, a crystal and a solution, but a solution is preferred. When crude phosphorothioate is in the form of a solution, the second step can be performed by easy operations as described below.

When crude phosphorothioate is in the form of a solution, it generally contains a hydrophobic organic solvent as a solvent.

Examples of the hydrophobic organic solvent include aromatic hydrocarbon solvents such as toluene and xylene; aliphatic hydrocarbon solvents such as hexane and heptane; ether solvents such as diethyl ether and methyl tert-butyl ether; halogenated hydrocarbon solvents such as dichloromethane, dichlorobenzene, and chlorobenzene; and ketone solvents such as methyl isobutyl ketone.

When crude phosphorothioate is in the form of a solution, it contains preferably an aromatic hydrocarbon, and more preferably toluene. When crude phosphorothioate contains an aromatic hydrocarbon, each operation can be performed more easily.

Crude phosphorothioate can be obtained by conventional processes, for example by condensing 2,6-dichloro-4-methylphenol and O,O-dimethyl chlorophosphorothioate in a solvent in the presence of copper chloride.

Crude phosphorothioate may be in the form of a solution of a reaction product obtained by a synthetic reaction of phosphorothioate; in the form of a crystal or a powder recovered from the solution of the reaction product; and a resultant obtained by an aftertreatment, such as concentration, of the solution of the reaction product. Such an aftertreatment is preferably performed at a temperature range in which phosphorothioate is not degraded, for example a range of 40° C. to 60° C.

In the present invention, a purified O-(2,6-dichloro-4-methylphenyl)-O,O-dimethyl phosphorothioate (hereinafter this is referred to as "purified phosphorothioate") is in the form of a powder, a crystal or a solution of phosphorothioate obtained by the production process of the present invention.

The process for producing a purified phosphorothioate of the present invention includes the first step of bringing crude phosphorothioate into contact with an acid.

In the first step, one or more acids may be used.

The acid may be any of an inorganic acid and an organic acid. But an inorganic acid is preferred since the treatment of discharged water produced in the second step is easy.

Examples of the inorganic acid include HCl, $H_2SO_4$, and phosphoric acid, and HCl is preferred.

Examples of the organic acid include acetic acid.

The acid may be any of an acid aqueous solution and a solid acid.

As the acid aqueous solution, preferred are those which the above-exemplified acids are dissolved in water.

When the acid is an acid aqueous solution, the acid concentration is preferably 0.1 to 10% by weight, and more preferably 0.1 to 3.5% by weight. The acid aqueous solution may contain an organic solvent as long as the solvent is present in a slight amount.

Examples of the solid acid include a cation exchange resin. Examples of the cation exchange resin include one having an acid group such as sulfonic acid or phosphonic acid as an exchange group and having a resin such as a styrene/divinylbenzene copolymer as a carrier.

The solid acid may be any of an organic solid acid and an inorganic solid acid.

In the first step, the amount of the acid to be used can be appropriately adjusted by considering the amounts of crude phosphorothioate and discharged water produced in each step and the like.

The contact of crude phosphorothioate with an acid can be carried out by, for example, the operations of the following (1) and (2):

(1) mixing crude phosphorothioate with an acid aqueous solution; and (2) mixing crude phosphorothioate with a solid acid.

In the operation (1), when crude phosphorothioate is in the form of a solution, the amount of an acid aqueous solution to be used is preferably 0.1 parts by weight or more, more preferably 0.1 to 1 part by weight, and still more preferably 0.1 to 0.5 parts by weight per 1 part by weight of crude phosphorothioate in that the contact operation is easy.

In the operation (1), when crude phosphorothioate is a powder or a crystal, the amount of an acid aqueous solution to be used is preferably 1 part by weight or more, and more preferably 1 to 10 parts by weight per 1 part by weight of crude phosphorothioate in that the contact operation is easy.

Examples of the operation (1) include an operation of mixing, with an aqueous solution of an inorganic acid, a crude phosphorothioate which contains an aromatic hydrocarbon solvent; and an operation of adding crude phosphorothioate, which is in the form of a powder or a crystal, to an acid aqueous solution and then stirring them.

The operation time of the above (1) can be set by considering the amounts and types of crude phosphorothioate and an acid aqueous solution, a stirrer to be used and the like. The operation time of the above (1) is preferably 15 to 60 minutes.

In the operation (2), when crude phosphorothioate is in the form of a solution, the amount of a solid acid to be used is preferably 0.1 to 1 part by weight, and more preferably 0.1 to 0.3 parts by weight per 1 part by weight of crude phosphorothioate in that the recovery of the solid acid is easy.

In the operation (2), when crude phosphorothioate is in the form of a powder or a crystal, it is preferred that the contact be carried out in the presence of a mixed solvent of an organic solvent and an aqueous solvent or an organic solvent, and it is more preferred that the contact be carried out in the presence of an aromatic hydrocarbon solvent. In the operation (2), when crude phosphorothioate, which is in the form of a powder or a crystal, is contacted in the presence of the mixed solvent or an organic solvent, these are preferably mixed so as to set the content of the crude phosphorothioate at 0.1 to 1 part by weight per 1 part by weight of the solvent. In the operation (2), when crude phosphorothioate is in the form of a powder or a crystal, the amount of a solid acid to be used is preferably 0.1 to 1 part by weight, and more preferably 0.1 to 0.3 parts by weight per 1 part by weight of crude phosphorothioate in that the recovery of the solid acid is easy.

Examples of the operation (2) include an operation of adding a solid acid to crude phosphorothioate dissolved in an organic solvent and then stirring them, and a method of passing crude phosphorothioate dissolved in an organic solvent through a column filled with a solid acid.

The operation time of the above (2) may be set by considering the amounts and types of crude phosphorothioate and a solid acid, a stirrer to be used and the like.

The contact of crude phosphorothioate with an acid can be carried out within a temperature range, which does not lead to degradation of phosphorothioate, evaporation of a solvent, and the like. The temperature of the contact is preferably at 0° C. to 90° C., and more preferably at 40° C. to 60° C.

As the first step, since the operation is easy, the operation (1) is preferred, an operation of mixing, with an aqueous solution of an inorganic acid, a crude phosphorothioate which contains an aromatic hydrocarbon solvent is more preferred, and an operation of mixing a crude phosphorothioate containing toluene with hydrochloric acid is still more preferred.

The process for producing a purified phosphorothioate of the present invention includes the second step of recovering purified phosphorothioate from the mixture obtained in the first step.

The mixture generally contains phosphorothioate and the acid used in the first step. The mixture may contain a hydrophobic organic solvent and water depending on the types of crude phosphorothioate and the acid used in the first step.

Purified phosphorothioate can be recovered as a solution by, for example, layer separation and a liquid separation operation.

The layer separation can be performed by leaving the mixture obtained in the first step to be still standing. The layer separation may be performed after adding a hydrophobic organic solvent and water to the mixture as required.

A layer of purified phosphorothioate and an aqueous layer containing an acid are formed by the layer separation. It can be visually confirmed that the layer of purified phosphorothioate and the aqueous layer are formed. The still standing time until the layer of purified phosphorothioate and the aqueous layer are separated can be also determined in advance by a preliminary experiment.

The layer of purified phosphorothioate can be recovered by a known process such as a liquid separation operation. The layer separation and liquid separation in the second step may be performed repeatedly. When the layer separation and liquid separation are performed repeatedly, generally, after adding further water to the layer recovered by a liquid separation operation, the resultant is stirred, left to stand and liquid-separated.

In the second step, purified phosphorothioate can be also recovered by performing operations such as concentration, reprecipitation or recrystallization in addition to the layer separation and liquid separation operation.

The process for producing phosphorothioate of the present invention includes

Step A of condensing 2,6-dichloro-4-methylphenol and O,O-dimethyl chlorophosphorothioate in a solvent in the presence of copper chloride;

Step B of bringing the reaction mixture obtained in the step A into contact with an acid; and Step C of recovering phosphorothioate from the mixture obtained in the step B.

A solvent in the step A is preferably an organic solvent, more preferably a hydrophobic organic solvent, and still more preferably an aromatic hydrocarbon solvent. As the aromatic hydrocarbon solvent, toluene is preferred.

In the step A, the amount of copper chloride to be used is preferably 0.005 to 0.02 mol per 1 mol of 2,6-dichloro-4-methylphenol.

The amount of the 2,6-dichloro-4-methylphenol to be used is preferably 1 to 1.5 mol and more preferably 1 to 1.1 mol per 1 mol of O,O-dimethyl chlorophosphorothioate.

Still, the step A is preferably performed in the presence of a base. Hydrogen chloride produced as a by-product can be neutralized by performing the step A in the presence of a base. The base is preferably an inorganic base, more preferably a base containing an alkali metal or an alkali earth metal, and still more preferably sodium hydroxide and potassium hydroxide. The amount of the base to be used can be suitably selected by, for example, the type and reaction scale of the base. Preferably, a 10 to 40% by weight aqueous solution of the base is prepared in advance and then added to the mixture containing 2,6-dichloro-4-methylphenol and O,O-dimethyl chlorophosphorothioate.

The step A can be performed under a temperature generally of 40° C. to 70° C. and preferably 40° C. to 60° C.

Phosphorothioate is produced by performing the step A.

The reaction mixture obtained in the step A contains phosphorothioate and a solvent.

The acid in the step B includes the same acids as those used in the process of producing purified phosphorothioate.

The contact of the reaction mixture obtained in step A with an acid, for example, can be performed by the following operations (I) and (II):

(I) mixing the reaction mixture with an acid aqueous solution; and (II) mixing the reaction mixture with a solid acid.

In the operation (I), the amount of an acid aqueous solution to be used is preferably 0.1 parts by weight or more, more preferably 0.1 to 1 part by weight, and still more preferably 0.1 to 0.5 parts by weight per 1 part by weight of the reaction mixture in that the contact operation is easy.

Examples of the operation (I) include an operation of mixing the reaction mixture with an aqueous solution of an inorganic acid.

The operation time of the above (I) can be set by considering the amounts and types of the reaction mixture and an acid aqueous solution, a stirrer to be used, and the like. The operation time of the above (I) is preferably 15 to 60 minutes.

In the operation (II), the amount of a solid acid to be used is preferably 0.1 to 1 part by weight, and more preferably 0.1 to 0.3 parts by weight per 1 part by weight of the reaction mixture obtained in step A in that the recovery of the solid acid is easy.

Examples of the operation (II) include an operation of adding a solid acid to the reaction mixture obtained in the step A and then stirring them, and a process of passing the reaction mixture through a column filled with a solid acid.

The operation time of the above (II) can be set by considering the amounts and types of the reaction mixture and a solid acid, a stirrer to be used, and the like.

The contact of the reaction mixture with an acid can be performed within a temperature range, which does not lead to degradation of phosphorothioate, evaporation of a solvent and the like. The temperature of the contact is preferably 0° C. to 90° C., and more preferably 40° C. to 60° C.

As the step B, since the operation is easy, the operation (I) is preferred and an operation of mixing the reaction mixture obtained in the step A with an aqueous solution of an inorganic acid is more preferred.

The mixture obtained in the step B generally contains phosphorothioate and the acid used in the step B.

In the step C, the phosphorothioate can be recovered by, for example, layer separation and a liquid separation operation. In the step C, operations such as concentration, reprecipitation or recrystallization in addition to the layer separation and liquid separation operation may be also performed. Specifically, each operation can be performed by the above-described procedures for the process of producing purified phosphorothioate of the present invention.

The solution, crystal and powder of phosphorothioate obtained by each production process of the present invention (hereinafter these are referred to as "phosphorothioate in the present invention") have more excellent heat stability than the solution, crystal and powder of the phosphorothioate obtained by a conventional production processes (hereinafter the solution, crystal and powder are referred to as "conventional phosphorothioate").

The reasons why phosphorothioate in the present invention exhibits excellent heat stability are assumed to be as follows. That is, conventional phosphorothioate is easily converted into O-(2,6-dichloro-4-methylphenyl)-O,S-dimethyl phosphate (hereinafter referred to as "S-methyl form") by heating treatment. On the other hand, phosphorothioate in the present invention is difficult to be converted into S-methyl form by heating treatment. That is, the structure of phosphorothioate in the present invention is not converted even by heating treatment.

If, for example, phosphorothioate in the present invention is heated at a temperature of 60° C. for 20 hours or more, the increased ratio of the content rates of S-methyl form (C1/C0) is usually 5 or less, which ratio is calculated with the content rate of S-methyl form prior to heating (C0) and that of S-methyl form after heating (C1).

The content rate of each S-methyl form is determined by gas chromatography.

The structure of phosphorothioate in the present invention is hardly converted even by heating treatment during formulation and storing under a high temperature.

EXAMPLES

Hereinafter, the present invention will be described by way of Examples, but the present invention is not limited thereto.

In Examples and Comparative Examples, each content rate of phosphorothioate and S-methyl form was determined by gas chromatography analysis of the solutions, which were prepared by diluting 0.5 g of a sample with 10 ml of chloroform, on the following conditions.

(Conditions of Analysis)

Column: capillary column (carrier: 5% phenylmethylpolysiloxane)

Carrier gas: helium

The content of phosphorothioate is an analysis value by the internal standard method.

The content rate of S-methyl form was calculated on the basis of the spectrum of gas chromatography by the following formula:

$$\text{Content rate of S-methyl form} = A_{sm}/(A_{sm}+A_{pt})$$

(wherein Asm represents the peak area value of S-methyl form, and Apt represents the peak area value of phosphorothioate).

Example 1

To crude phosphorothioate containing phosphorothioate and toluene (content of phosphorothioate: 48.2% by weight, about 180 g), 42.3 g of 0.6% by weight hydrochloric acid was added, followed by stirring them for 30 minutes. The resulting mixed liquid was separated into layers by being left to stand, and the formed aqueous layer was removed to obtain purified phosphorothioate (content of phosphorothioate: 48.7% by weight).

The content rate of S-methyl form in the purified phosphorothioate was 0.02% (C0).

The purified phosphorothioate was treated by heating at a temperature of 60° C. for 96 hours. The content rate of S-methyl form in the purified phosphorothioate after heating was 0.09% (C1) and the increased ratio of the content rates of S-methyl form (C1/C0) was 4.5.

Example 2

To crude phosphorothioate containing phosphorothioate and toluene (content of phosphorothioate: 48.2% by weight, about 180 g), 42.3 g of 0.3% by weight hydrochloric acid was added, followed by stirring them for 30 minutes. The resulting mixed liquid was separated into layers by being left to stand and the formed aqueous layer was removed to obtain purified phosphorothioate (content of phosphorothioate: 48.7% by weight).

The content rate of S-methyl form in the purified phosphorothioate was 0.03% (C0).

The purified phosphorothioate was treated by heating at a temperature of 60° C. for 23 hours.

The content rate of S-methyl form in the purified phosphorothioate after heating was 0.04% (C1) and the increased ratio of the content rates of S-methyl form (C1/C0) was 1.3.

Comparative Example 1

The same experiments as in Example 1 were repeated except that water was used in place of 0.6% by weight hydrochloric acid. For the obtained toluene solution containing phosphorothioate, the content rate of S-methyl form was 0.02% (C0), the content rate of S-methyl form after heating treatment at a temperature of 60° C. for 96 hours was 1.99% (C1) and the increased ratio of the content rates of S-methyl form (C1/C0) was 99.5.

Comparative Example 2

The same experiments as in Example 2 were repeated except that water was used in place of 0.3% by weight hydrochloric acid. For the obtained toluene solution containing phosphorothioate, the content rate of S-methyl form was 0.04% (C0), the content rate of S-methyl form after heating treatment at a temperature of 60° C. for 23 hours was 0.85% (C1) and the increased ratio of the content rates of S-methyl form (C1/C0) was 21.3.

Example 3

In a five-necked separable flask equipped with a stirrer, a thermometer and a condenser, 69.7 g of an O,O-dimethyl chlorophosphorothioate solution (toluene solution, content 76.5% by weight), 98.1 g of a 2,4-dichloro-4-methylphenol solution (toluene solution, content 64.6% by weight) and 24.4 g of toluene were charged, and then heated to 45° C. After that, 0.2 g of copper (I) chloride was charged, and then, 50.4 g of a 27% by weight aqueous sodium hydroxide solution was dropped thereto at an inside temperature of 45° C. to 50° C. for 3 hours. The resultant was maintained at the same temperature for an hour, and then 3.7 g of water, 38.0 g of toluene and 60.0 g of a 27% by weight aqueous sodium hydroxide solution were added, followed by maintaining the resultant at the same temperature for another 30 minutes. The reaction solution was transferred to a separating funnel, and the aqueous layer was removed by liquid separation to recover the organic layer. It confirmed that the organic layer contained 48.2% by weight phosphorothioate.

To about 180 g of the organic layer, 42.3 g of 0.6% by weight hydrochloric acid was added, followed by stirring them for 30 minutes. The resulting mixed liquid was separated into layers by being left to stand. The formed aqueous layer was removed to obtain a toluene solution containing 48.7% by weight phosphorothioate.

Example 4

In a five-necked separable flask equipped with a stirrer, a thermometer and a condenser, 69.7 g of an O,O-dimethyl chlorophosphorothioate solution (toluene solution, content 76.5% by weight), 112.2 g of a 2,4-dichloro-4-methylphenol solution (toluene solution, content 58.3% by weight) and 10.0 g of toluene were charged, and then heated to 45° C. After that, 0.2 g of copper (I) chloride was charged, and then, 50.4 g of a 27% by weight aqueous sodium hydroxide solution was dropped thereto at an inside temperature of 45° C. to 50° C. for 3 hours. The resultant was maintained at the same temperature for an hour, and then 3.7 g of water, 38.0 g of toluene and 53.2 g of a 27% by weight aqueous sodium hydroxide solution were added, followed by maintaining the resultant at the same temperature for another 30 minutes. The reaction solution was transferred to a separating funnel and the aqueous layer was removed by liquid separation to recover the organic layer. It confirmed that the organic layer contained 48.2% by weight phosphorothioate.

To about 180 g of the organic layer, 42.3 g of 0.3% by weight hydrochloric acid was added, followed by stirring them for 30 minutes. Thereto, 42.3 g of 0.3% by weight hydrochloric acid was added, followed by stirring them for 30 minutes. The resulting mixed liquid was separated into layers by being left to stand. The formed aqueous layer was removed to obtain a toluene solution containing 48.7% by weight phosphorothioate.

INDUSTRIAL APPLICABILITY

Phosphorothioate obtained by the present invention exhibits excellent heat stability. Thus, the formulation of a soil fungicide and the like can be more easily performed.

The invention claimed is:
1. A process for producing a purified O-(2,6-dichloro-4-methylphenyl)-O,O-dimethyl phosphorothioate, the process comprising:
   a first step of bringing a crude O-(2,6-dichloro-4-methylphenyl)-O,O-dimethyl phosphorothioate into contact with hydrochloric acid; and
   a second step of recovering the purified O-(2,6-dichloro-4-methylphenyl)-O,O-dimethyl phosphorothioate from the mixture obtained in the first step.
2. The production process according to claim 1, wherein the crude O-(2,6-dichloro-4-methylphenyl)-O,O-dimethyl phosphorothioate contains an aromatic hydrocarbon solvent.
3. The production process according to claim 1, wherein the first step is performed by mixing a crude O-(2,6-dichloro-4-methylphenyl)-O,O-dimethyl phosphorothioate containing an aromatic hydrocarbon solvent with an aqueous solution of hydrochloric acid.
4. The production process according to claim 1, wherein the crude O-(2,6-dichloro-4-methylphenyl)-O,O-dimethyl phosphorothioate is obtained by bringing 2,6-dichloro-4-methylphenol into contact with O,O-dimethyl chlorophosphorothioate in a solvent in the presence of copper chloride.

* * * * *